United States Patent [19]

Venkateshwaran et al.

[11] Patent Number: 5,445,607
[45] Date of Patent: Aug. 29, 1995

[54] IONTOPHORESIS DEVICE AND METHOD USING A RATE-CONTROLLING ELECTRICALLY SENSITIVE MEMBRANE

[75] Inventors: Srinivasan Venkateshwaran; Daniel C. H. Cheng, both of Salt Lake City, Utah

[73] Assignee: TheraTech, Inc., Salt Lake City, Utah

[21] Appl. No.: 962,030

[22] Filed: Oct. 15, 1992

Related U.S. Application Data

[63] Continuation of Ser. No. 427,069, Oct. 23, 1989, abandoned.

[51] Int. Cl.$^6$ .............................................. A61N 1/30
[52] U.S. Cl. ................................. 604/20; 601/148; 601/15
[58] Field of Search .................... 128/802, 803, 798; 604/20

[56] References Cited

U.S. PATENT DOCUMENTS

| | | | |
|---|---|---|---|
| 3,598,122 | 8/1971 | Zaffaroni | 604/20 |
| 3,966,934 | 6/1976 | Adams et al. | 424/251 |
| 3,989,816 | 11/1976 | Rajadhyaksha | 424/60 |
| 4,006,218 | 2/1977 | Sipos | 424/54 |
| 4,166,457 | 9/1979 | Jacobsen et al. | 604/20 |
| 4,419,092 | 12/1983 | Jacobsen et al. | 604/20 |
| 4,557,723 | 12/1985 | Sibalis | 604/20 |
| 4,568,343 | 2/1986 | Leeper et al. | 604/20 |
| 4,640,689 | 2/1987 | Sibalis | 604/20 |
| 4,722,726 | 2/1988 | Sanderson et al. | 604/20 |
| 4,731,049 | 3/1988 | Parsi | 604/20 |
| 4,744,787 | 5/1988 | Phipps et al. | 604/20 |
| 4,746,515 | 5/1988 | Cheng et al. | 424/449 |
| 4,752,285 | 6/1988 | Petelenz et al. | 604/20 |
| 4,764,379 | 8/1988 | Sanders et al. | 424/449 |
| 4,781,924 | 11/1988 | Lee et al. | 424/449 |
| 4,786,277 | 11/1988 | Powers et al. | 604/20 |
| 4,808,172 | 2/1989 | Murata | 604/306 |
| 4,820,720 | 4/1989 | Sanders et al. | 424/449 |
| 4,830,855 | 5/1989 | Stewart . | |
| 4,837,027 | 6/1989 | Lee et al. | 424/486 |
| 4,846,826 | 7/1989 | Shaw et al. | 604/890.1 |
| 4,849,226 | 7/1989 | Gale | 424/448 |
| 4,927,408 | 5/1990 | Haak et al. | 604/20 |
| 4,940,456 | 7/1990 | Sibalis et al. | 604/20 |
| 5,019,034 | 5/1991 | Weaver et al. | 604/20 |
| 5,080,646 | 1/1992 | Theeuwes et al. | 604/20 |
| 5,135,480 | 8/1992 | Bannon et al. | 604/20 |

FOREIGN PATENT DOCUMENTS

| | | |
|---|---|---|
| 0043738 | 1/1982 | European Pat. Off. . |
| 0261429 | 3/1988 | European Pat. Off. . |
| 0272987 | 6/1988 | European Pat. Off. . |
| 0318385 | 11/1988 | European Pat. Off. . |
| 2562800 | 10/1985 | France . |

OTHER PUBLICATIONS

Lattin, Gary A. "Method to Control Delivery of Uncharged Drugs Via Iontophoresis" Nov., 1988.

*Primary Examiner*—John D. Yasko
*Assistant Examiner*—Adam J. Cermak
*Attorney, Agent, or Firm*—Morrison & Foerster

[57] ABSTRACT

An iontophoresis device comprising a drug reservoir containing the drug in ionic form and in communication with the skin, a skin permeation enhancing agent contained in the reservoir or in a second reservoir also in communication with the skin, an electrode in contact with the drug, another electrode in contact with the skin, a D.C. power source connected to the electrodes and an electrically sensitive membrane interposed between the reservoir and the skin that is impermeable to drug in the absence of a voltage difference between the electrodes and permeable to the drug in the presence of a voltage difference. The skin permeation enhancing agent eliminates the skin as a rate-controlling element, thus making the rate of drug administration dependent upon the membrane permeability, which in turn is controlled electrically.

3 Claims, 1 Drawing Sheet

IONTOPHORESIS DEVICE AND METHOD USING A RATE-CONTROLLING ELECTRICALLY SENSITIVE MEMBRANE

This application is a continuation of application Ser. No. 07/427,069, filed Oct. 23, 1989, now abandoned.

TECHNICAL FIELD

This invention is in the field of transdermal drug delivery. More particularly it relates to the iontophoretic administration of drugs through the skin.

BACKGROUND

Iontophoresis is a well-known manner of administering drugs through the skin. See, for instance, U.S. Pat. Nos. 4,744,787, 4,722,726, 4,731,049 and 4,752,285.

The use of rate-controlling membranes in the passive (non-iontophoretic) administration of drugs transdermally is described in U.S. Pat. Nos. 3,598,122, 3,797,444 and 3,966,934.

The use of skin permeation enhancers to increase the permeability of skin to drugs is well known. See, for instance, U.S. Pat. Nos. 4,006,218, 4,568,343, 4,746,515, 3,989,816, 4,316,893, 4,764,379 and EP Publications 272,987, 261,429 and 043738.

DISCLOSURE OF THE INVENTION

One aspect of the invention is a device for administering a drug transdermally through a predetermined area of skin in a therapeutically effective regimen, said drug being one that will not permeate passively through said area of skin at a therapeutically effective level comprising:

(a) a reservoir containing the drug adapted to be placed in communication with the area of skin;

(b) means for enhancing the permeability of the area of skin to the drug to a level at which the skin is substantially permeable to the drug;

(c) a stimulus-sensitive membrane interposed between the reservoir and the skin, said membrane being substantially impermeable to the drug when not subjected to said stimulus and permeable to the drug when subjected to the stimulus; and (d) means for applying said stimulus to said membrane, whereby said regimen is dependent on the characteristics of said stimulus.

Another aspect of the invention is a device for administering a drug iontophoretically through a predetermined area of skin in a therapeutically effective regimen comprising:

(a) a reservoir of said drug in a form susceptible to iontophoretic administration in communication with said area of skin;

(b) a skin permeation enhancing agent contained within said reservoir or in a second reservoir that is also in communication with the skin;

(c) a first electrode in communication with said reservoir;

(d) a second electrode in communication with the skin at a location separated from said area of skin;

(e) means for creating an electric voltage difference between the first and second electrodes; and (f) an electrically sensitive membrane interposed between said reservoir and the area of skin that is substantially impermeable to the drug when the voltage difference is absent and is permeable to the drug when the voltage difference is present.

Still another aspect of the invention is a method of administering a drug iontophoretically through a predetermined area of the skin of a patient comprising: placing a reservoir of a solution of the drug in communication with said area of skin, said reservoir having a first electrode in electrical communication therewith; placing a second electrode in communication with the skin at a location separated from said area; and creating a voltage difference between the first and second electrodes, characterized in that a skin permeation enhancer is applied to the skin to make the skin substantially permeable to the drug and an electrically sensitive membrane is interposed between the reservoir and the area of skin, the membrane being substantially impermeable to the drug in the absence of the voltage difference and permeable to the drug in the presence of the voltage difference.

MODES FOR CARRYING OUT THE INVENTION

Figure 1:
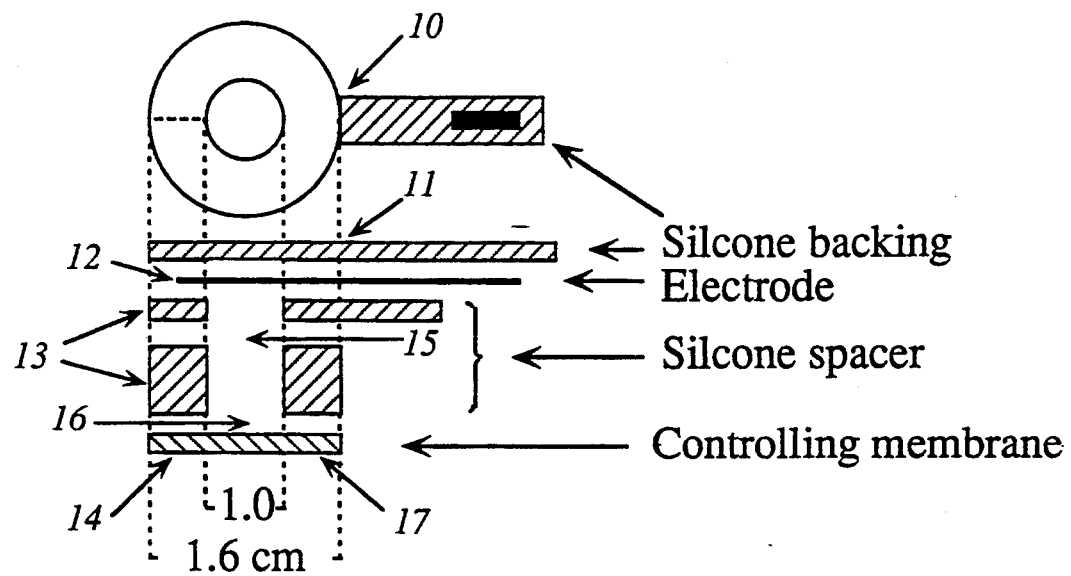
FIG. 1 is an exploded view of an embodiment of the invention device.

FIG. 1 depicts an iontophoresis device, generally designated 10. Device 10 consists of a impermeable backing sheet 11 (such as Dow Corning silastic sheeting), an electrode 12, an impermeable spacer element 13 which can be made of the same material as backing 11, and an electrically sensitive membrane 14. In one embodiment of this device that was used to deliver the model drug TEAB (($CH_3CH_2$)$_4$—$N^+$.$Br^-$), a membrane made of 25 micrometer thick laminate of cellophane coated with polyvinylchloride or saran to render the surface hydrophobic was used. The cylindrical space 15 within the spacer is filled with a formulation of the drug in ionic form (solution or gel), designated 16 in FIG. 1.

Figure 2:
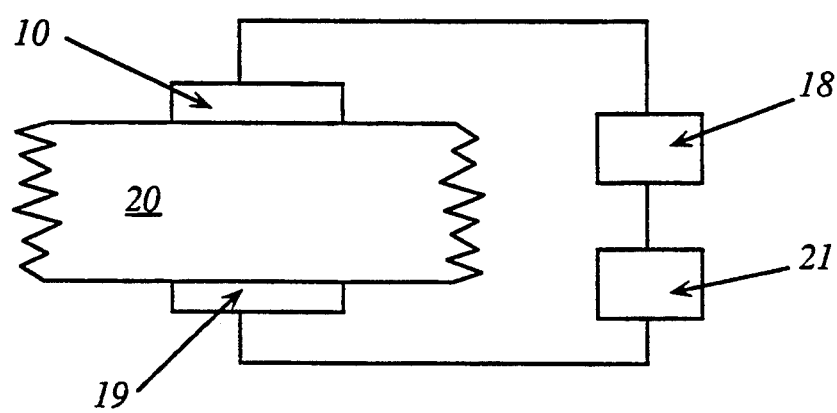
FIG. 2 is a schematic showing the placement of the device on the skin.

In use, device 10 is placed on the skin with the basal surface 17 of the membrane in contact with the skin. If desired, the device can be affixed to the skin by means of an adhesive overlay (not shown) or a layer or peripheral ring of drug-permeable adhesive on the basal surface of the membrane (not shown). Electrode 12 is then connected to a battery or other D.C. power source 18 (FIG. 2). The polarity of electrode 12 will depend upon the charge of the ion species of drug. The drug and electrode 12 should be of the same charge. A second electrode 19 (FIG. 2) is placed in contact with the skin 20 at a location separated from electrode 12. Electrode 19 is connected to the opposite pole of the power source. The circuit preferably includes conventional switching, voltage regulation and timing means, schematically designated 21, to control the duration and magnitude of the voltage difference across the electrodes.

A central feature of this invention is the employment of membrane 14 as an element that monitors the rate at which the drug is administered to the patient. In order for this to happen two conditions must be met. First, the skin itself must not be a rate-controlling barrier to delivery of the drug from the device through to circulation. To achieve this condition, a skin permeation enhancing agent is applied to the area of skin through which the drug is administered. That application may be made prior to or concurrently with the drug administration.

When administered concurrently, the enhancer is included as a component of the device. For instance, the enhancer may be contained in the reservoir with the drug or in a second reservoir layer that either overlies or underlies the membrane, depending upon whether the membrane is permeable to the enhancer. Normally, if the membrane is impermeable to the enhancer, the enhancer will be contained in a second, underlying reservoir layer. Alternatively in such instances, and depending upon the particular enhancer used, the drug ions may act as carriers to transport the enhancer through the membrane. Examples of permeations are given in the patents and patent publications mentioned above.

The second condition is that the membrane be electrically sensitive; that is, the membrane is substantially impermeable to the drug in the absence of the voltage difference across the electrodes and permeable when the difference is applied. Accordingly, the pattern of drug delivery is essentially controlled by the permeability of the membrane to the drug, which, in turn is controlled electrically. Thus, by manipulation of the switching/voltage regulation/timing means in the circuit, an infinite variety of temporal or preprogrammed closing regimens may be achieved. Zero order (constant rate) release rate is achieved by keeping the current through the circuit constant and the transference number of the drug ion constant. In general, the rate of administration increases with increasing current.

Preferably, the electrodes are silver-silver chloride. Examples of other electrodes used in iontophoresis devices are described at col. 5 of U.S. Pat. No. 4,744,787.

The backing and spacer element may be made from drug impermeable materials such as those described in the patents cited above.

The conditions, e.g., voltage difference, current, pH at electrodes, used to administer drugs iontophoretically are described in the patents cited above.

While the invention has been described specifically in terms of an embodiment that employs a membrane whose permeability is sensitive to electricity, it will be appreciated that membranes whose permeability is sensitive to other types of energy such as heat, radiation, microwave or sonic energy, may be used in place of the electrically sensitive membrane and the energy source altered accordingly.

We claim:

1. A device for administering a drug transdermally through a predetermined area of skin in a therapeutically effective regimen, said drug being one that will not permeate passively through said area of skin at a therapeutically effective level comprising:
    (a) a reservoir containing the drug adapted to be placed in communication with the area of skin;
    (b) means for enhancing the permeability of the area of skin to the drug to a level at which the skin is substantially permeable to the drug;
    (c) a stimulus-sensitive membrane interposed between the reservoir and the skin, said membrane having a hydrophobic surface and being substantially impermeable to the drug when not subjected to said stimulus and permeable to the drug when subjected to the stimulus said stimulus not affecting the form of the drug; and
    (d) means for applying said stimulus to said membrane, whereby said regimen is dependent on the presence, absence, or magnitude characteristics of said stimulus.

2. A device for administering a drug iontophoretically through a predetermined area of skin in a therapeutically effective regimen:
    (a) a reservoir of said drug in a form susceptible to iontophoretic administration in communication with said area of skin, said drug being one that will not permeate passively through said area of skin at a therapeutically effective level;
    (b) a skin permeation enhancing agent that enhances the permeability of the area of skin to a level at which the skin is substantially permeable to the drug, said permeation enhancing agent contained within said reservoir that is also in communication with the skin;
    (c) a first electrode in communication with said reservoir;
    (d) a second electrode in communication with the skin at a location separated from said area of skin;
    (e) means for creating an electric voltage difference between the first and second electrodes; and
    (f) an electrically sensitive membrane interposed between said reservoir and the area of skin that has a hydrophobic surface and is substantially impermeable to the drug when the voltage difference is absent and is permeable to the drug when the voltage difference is present.

3. In a method of administering a drug iontophoretically through a predetermined area of the skin of a patient comprising placing a reservoir of a solution of the drug in communication with said area of skin, said reservoir having a first electrode in electrical communication therewith, placing a second electrode in communication with the skin at a location separated from said area, and creating a voltage difference between the first and second electrodes, said drug being one that will not permeate passively through said area of skin at a therapeutically effective level, the improvement wherein a skin permeation enhancer is applied to the skin to make the skin substantially permeable to the drug and an electrically sensitive membrane having a hydrophobic surface is interposed between the reservoir and the area of skin, the membrane being substantially impermeable to the drug in the absence of the voltage difference and permeable to the drug in the presence of the voltage difference.

* * * * *